(12) United States Patent
Chehade

(10) Patent No.: US 12,220,543 B2
(45) Date of Patent: Feb. 11, 2025

(54) ELONGATED MEDICAL CATHETER INCLUDING MARKER BAND

(71) Applicant: Boston Scientific Medical Device Limited, Ballybrit (IE)

(72) Inventor: Moussa Chehade, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 38 days.

(21) Appl. No.: 17/411,178

(22) Filed: Aug. 25, 2021

(65) Prior Publication Data

US 2022/0072274 A1  Mar. 10, 2022

Related U.S. Application Data

(60) Provisional application No. 63/076,535, filed on Sep. 10, 2020.

(51) Int. Cl.
*A61M 25/01* (2006.01)

(52) U.S. Cl.
CPC . *A61M 25/0108* (2013.01); *A61M 2025/0166* (2013.01)

(58) Field of Classification Search
CPC ..... A61F 2/95; A61F 2/06; A61F 2/82; A61B 1/018; A61B 34/20; A61B 90/96; A61B 90/39; A61L 31/14; A61L 31/022; A61L 31/18; C22C 19/07; C22C 1/045; C22C 1/0433

See application file for complete search history.

(56) References Cited

U.S. PATENT DOCUMENTS

| | | | |
|---|---|---|---|
| 175,254 | A | 3/1876 | Oberly |
| 827,626 | A | 7/1906 | Gillet |
| 848,711 | A | 4/1907 | Daniel |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |
| 4,129,129 | A | 12/1978 | Amrine |
| 4,244,362 | A | 1/1981 | Anderson |
| 4,401,124 | A | 8/1983 | Guess et al. |
| 4,639,252 | A | 1/1987 | Kelly et al. |
| 4,641,649 | A | 2/1987 | Walinsky et al. |
| 4,669,467 | A | 6/1987 | Willett et al. |
| 4,682,596 | A | 7/1987 | Bales et al. |
| 4,790,311 | A | 12/1988 | Ruiz |
| 4,790,809 | A | 12/1988 | Kuntz |
| 4,793,350 | A | 12/1988 | Mar et al. |
| 4,807,620 | A | 2/1989 | Strul et al. |
| 4,832,048 | A | 5/1989 | Cohen |
| 4,840,622 | A | 6/1989 | Hardy |

(Continued)

*Primary Examiner* — Shahdeep Mohammed
(74) *Attorney, Agent, or Firm* — Nelson Mullins Riley & Scarborough LLP

(57) ABSTRACT

An elongated medical catheter includes a marker band with sidebands. The elongated medical catheter and the marker band have a radiopacity being different from the radiopacity of the sidebands.

15 Claims, 2 Drawing Sheets

(56) References Cited

U.S. PATENT DOCUMENTS

| | | |
|---|---|---|
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | Mcgee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B2 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |

(56) References Cited

U.S. PATENT DOCUMENTS

| | | |
|---|---|---|
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,592,100 B2 * | 3/2017 | Olson .................. A61B 34/20 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | MaGuire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0176682 A1 * | 9/2004 | Murphy .................. A61F 2/95 600/585 |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0113686 A1 * | 5/2005 | Peckham .................. A61F 2/06 600/431 |
| 2005/0119556 A1 | 6/2005 | Gillies et al. |
| 2005/0137527 A1 | 6/2005 | Kunin |
| 2005/0143770 A1 * | 6/2005 | Carter .................. A61F 2/95 606/1 |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2016/0250444 A1 * | 9/2016 | Lampropoulos .. A61M 25/0108 600/486 |
| 2017/0095646 A1 * | 4/2017 | Norman ............ A61M 25/0054 |
| 2017/0333149 A1 * | 11/2017 | Stigall ............... A61M 25/0108 |
| 2019/0021763 A1 | 1/2019 | Zhou et al. |
| 2019/0247035 A1 | 8/2019 | Gittard et al. |
| 2020/0038207 A1 * | 2/2020 | Simpson .................. A61L 31/14 |
| 2021/0106308 A1 * | 4/2021 | Stigall .................... A61B 90/39 |

* cited by examiner

SECTION A-A

ELONGATED MEDICAL CATHETER INCLUDING MARKER BAND

TECHNICAL FIELD

This document relates to the technical field of (and is not limited to) an elongated medical catheter including a marker band (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with existing (known) medical catheters. After much study of, and experimentation with, the existing (known) medical catheters, an understanding (at least in part) of the problem and its solution have been identified (at least in part) and are articulated (at least in part) as follows:

Known medical catheters (such as, known intravascular catheters, etc.) include at least one or more radiopaque marker bands (also called stripes) configured to indicate at least one position reference on the known intravascular catheters. The radiopaque marker bands are configured to be visible (detectable) under fluoroscopic imaging (by a fluoroscopic imaging system). The catheter material is loaded with (includes) a radiopaque material configured to improve visibility under fluoroscopic imaging. This is done because the materials (such as plastics) used in the known catheters may be inherently difficult to detect (see) under fluoroscopic imaging. There are physical constraints on the extent (strength) of radiopaque, and they may sometimes be challenging to visualize (under fluoroscopic imaging) in the clinic especially in small instances of the known catheters. A known method of improving visibility is to increase the visual contrast between the radiopaque marker band and the body of the known medical catheter. While this arrangement may be done by decreasing the overall radiopacity of the entire known catheter, this has the drawback of making the rest of the known catheter more difficult to visualize (under fluoroscopic imaging).

To mitigate, at least in part, at least one problem associated with the existing technology, there is provided (in accordance with a major aspect) an apparatus. The apparatus includes and is not limited to (comprises) an elongated medical catheter including a marker band with sidebands. The elongated medical catheter and the marker band have a radiopacity that is different from the radiopacity of the sidebands.

To mitigate, at least in part, at least one problem associated with the existing technology, there is provided (in accordance with a major aspect) an apparatus. The apparatus includes and is not limited to (comprises) an elongated medical catheter having a catheter distal portion and a catheter proximal portion. A marker band is positioned between the catheter distal portion and the catheter proximal portion. A first sideband is positioned proximate to the marker band. A second sideband is positioned proximate to the marker band. The radiopacity of the elongated medical catheter and the marker band is different from the radiopacity of the first sideband and the second sideband.

To mitigate, at least in part, at least one problem associated with the existing technology, there is provided (in accordance with a major aspect) a method. The method is for using an elongated medical catheter including a marker band with sidebands. The elongated medical catheter and the marker band have a radiopacity that is different from the radiopacity of the sidebands. The method includes and is not limited to (comprises) using the elongated medical catheter with a medical imaging system.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
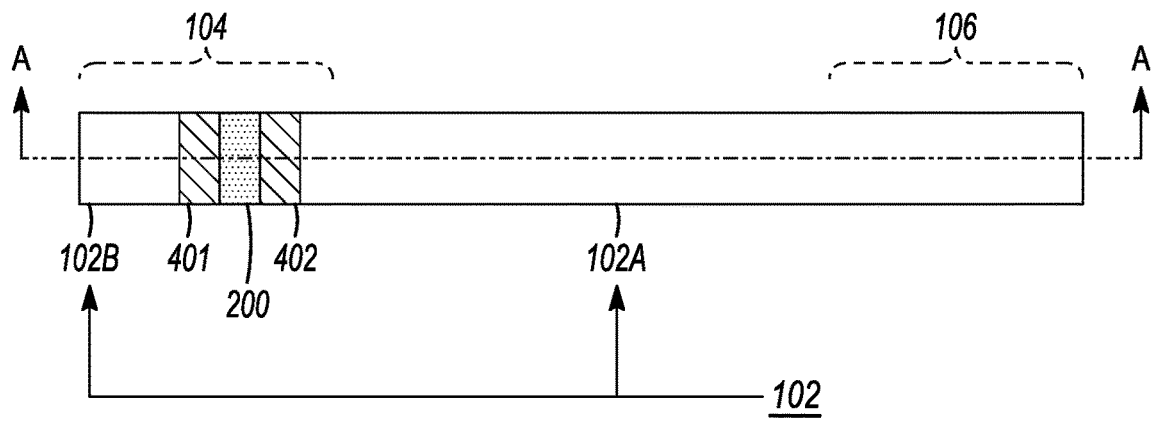
FIG. 1 and FIG. 2 depict a side view (FIG. 1) and a cross-sectional view (FIG. 2) of embodiments (implementations) of an elongated medical catheter.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

| LISTING OF REFERENCE NUMERALS USED IN THE DRAWINGS | |
|---|---|
| elongated medical catheter | 102 |
| first catheter section | 102A |
| second catheter section | 102B |
| catheter lumen | 103 |
| catheter distal portion | 104 |
| catheter proximal portion | 106 |
| marker band | 200 |
| first end portion | 301 |
| second end portion | 302 |
| first sideband | 401 |

-continued

LISTING OF REFERENCE NUMERALS
USED IN THE DRAWINGS

| second sideband | 402 |
| sidebands | (401, 402) |
| jig assembly | 900 |
| heat | 902 |
| heater | 904 |

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 2:
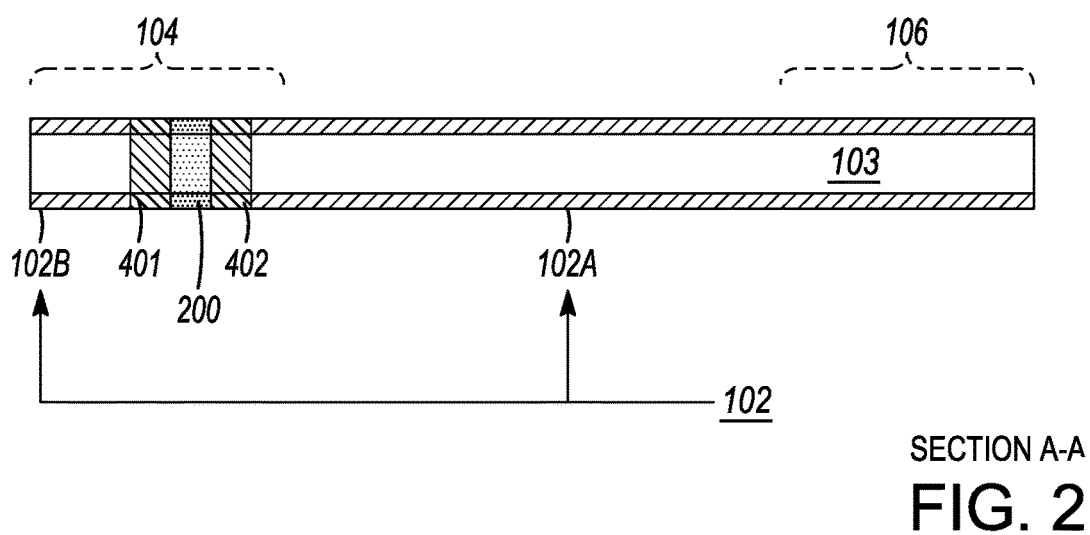

FIG. 1 and FIG. 2 depict a side view (FIG. 1) and a cross-sectional view (FIG. 2) of embodiments (implementations) of an elongated medical catheter 102.

Referring to the embodiment (implementation) as depicted in FIG. 1, the elongated medical catheter 102 includes a marker band 200 with sidebands (401, 402). The elongated medical catheter 102 and the marker band 200 have a radiopacity that is different from the radiopacity of the sidebands (401, 402). Radiopacity or radiodensity is opacity to the radio wave and/or X-ray portion of the electromagnetic spectrum: that is, the relative inability of those kinds of electromagnetic radiation to pass through a particular material. The elongated medical catheter 102 includes a marker band 200 with sidebands (401, 402) that have a sufficient degree of radiopacity such that a medical imaging system is able to detect these components. The sidebands (401, 402) are, preferably, positioned on opposite sides of the marker band 200; it will be appreciated that the sidebands (401, 402) may be positioned either proximate to the opposite sides of the marker band 200, or somewhat further away (if so desired). The elongated medical catheter 102 defines a catheter lumen 103 extending along a longitudinal axis of the elongated medical catheter 102. The elongated medical catheter 102 is configured to be inserted into a confined space defined by a living body (the patient).

Referring to the embodiment (implementation) as depicted in FIG. 1, the elongated medical catheter 102 includes biocompatible material properties suitable for specific performance (such as, electric dielectric strength, electric insulation, corrosion, water resistance, heat resistance, etc.) for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment (implementation) as depicted in FIG. 1, the elongated medical catheter 102 has, preferably a catheter distal portion 104 and a catheter proximal portion 106. The catheter distal portion 104 and the catheter proximal portion 106 are spaced apart from each other. The marker band 200 is, preferably, positioned between the catheter distal portion 104 and the catheter proximal portion 106. The sidebands (401, 402) include, for instance, a first sideband 401 and a second sideband 402. The first sideband 401 is positioned proximate to the marker band 200 (preferably, to one side of the marker band 200). The second sideband 402 is positioned proximate to the marker band 200 (preferably, to the other side of the marker band 200). The radiopacity of the elongated medical catheter 102 and the marker band 200 is different from the radiopacity of the first sideband 401 and the second sideband 402; this is done, preferably, in such a way that there is a contrast set up (between selected components of the elongated medical catheter 102, in which the contrast may be (readily) detected by a compatible medical-imaging system (such as, an x-ray system etc.).

Referring to the embodiment (implementation) as depicted in FIG. 1, the elongated medical catheter 102 includes a first catheter section 102A and a second catheter section 102B. The first catheter section 102A is positioned proximate to the first sideband 401. The second catheter section 102B is positioned proximate to the second sideband 402.

Referring to the embodiment (implementation) as depicted in FIG. 2, the catheter lumen 103 extends through the first sideband 401, the second sideband 402 and the marker band 200. More preferably, the catheter lumen 103 extends through the first sideband 401, the second sideband 402, the marker band 200, the first catheter section 102A and the second catheter section 102B.

Figure 3:
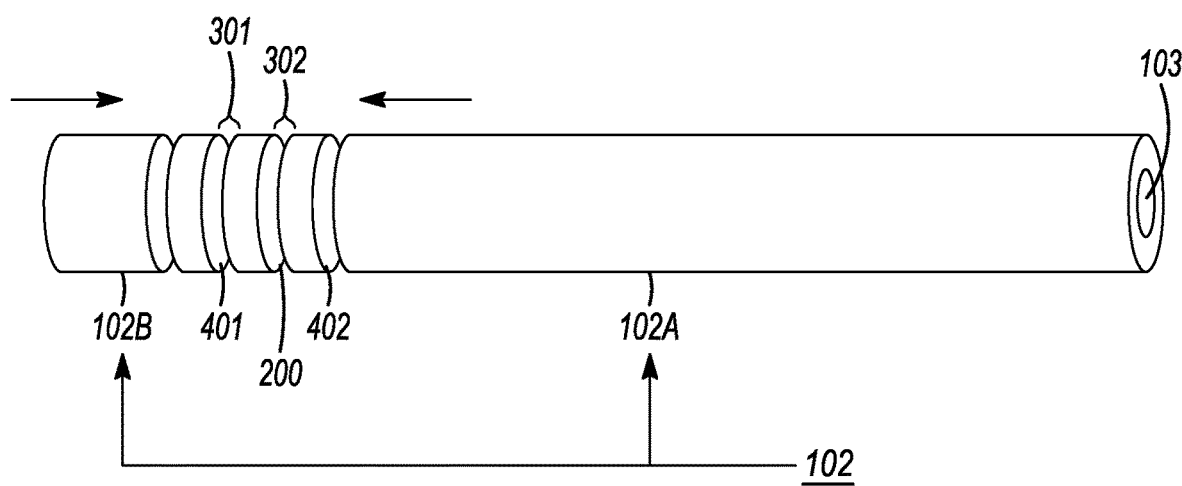
FIG. 3, FIG. 4 and FIG. 5 depict perspective views of embodiments (implementations) of the elongated medical catheter of FIG. 1.
Figure 4:
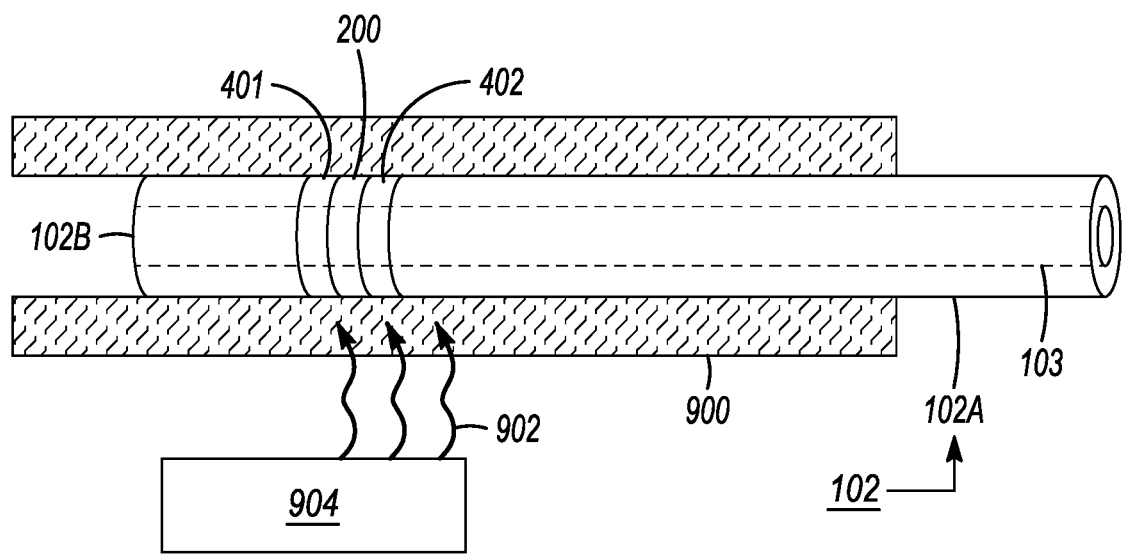
Figure 5:
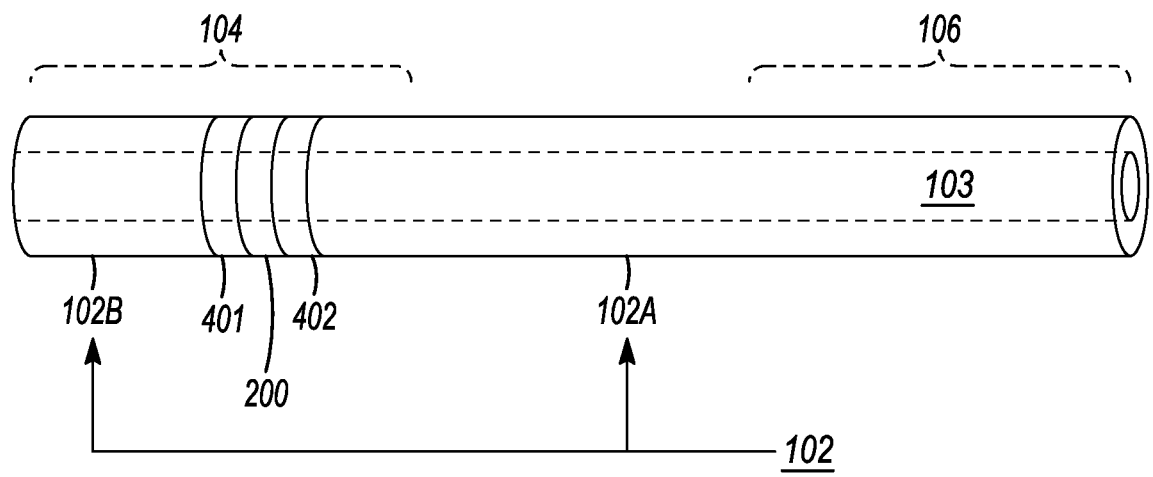

FIG. 3, FIG. 4 and FIG. 5 depict perspective views of embodiments (implementations) of the elongated medical catheter 102 of FIG. 1.

Referring to the embodiment (implementation) as depicted in FIG. 3, the marker band 200 has a first end portion 301 and a second end portion 302. The first end portion 301 and the second end portion 302 are spaced apart from each other. The first sideband 401 is positioned proximate to the first end portion 301 of the marker band 200. The second sideband 402 is positioned proximate to the second end portion 302 of the marker band 200. The elongated medical catheter 102 has a catheter radiopacity. The marker band 200 has a marker-band radiopacity. The first sideband 401 has a first sideband radiopacity. The second sideband 402 has a second sideband radiopacity. The first sideband radiopacity of the first sideband 401 is less than the catheter radiopacity of the catheter 102. The second sideband radiopacity of the second sideband 402 is less than the marker-band radiopacity of the marker band 200. It will be appreciated that an equivalent to "less than" may include "different from".

Referring to the embodiment (implementation) as depicted in FIG. 3, a first step in the manufacturing the of the elongated medical catheter 102 includes positioning the first sideband 401, the second sideband 402, the marker band 200, the first catheter section 102A and the second catheter section 102B in a spaced apart coaxial relationship.

Referring to the embodiment (implementation) as depicted in FIG. 4, a second step in the manufacturing the of the elongated medical catheter 102 includes positioning the first sideband 401, the second sideband 402, the marker band 200, the first catheter section 102A and the second catheter section 102B in an alignment relationship for insertion into an elongated jog assembly 900. The elongated jog assembly 900 is configured to securely hold these components while the components are attached to each other. Once these components are attached to each other, the lumen may be formed to extend through these components, etc.

Referring to the embodiment (implementation) as depicted in FIG. 4, a third step in the manufacturing the of the elongated medical catheter 102 includes applying heat 902 (via a heater 904) to the first sideband 401, the second sideband 402, the marker band 200, the first catheter section 102A and the second catheter section 102B after these components are positioned into the elongated jog assembly 900. The application of heat (or any type of suitable bonding method) is done in such a way that the segments become bonded to neighboring segments by melting these segments together so that they end up behaving as one piece of tubing. Gluing the segments together may be possible but might be less practical.

Referring to the embodiment (implementation) as depicted in FIG. 5, the amount of heat and the time for application of such heat should be enough to bond the second catheter section 102B with the first sideband 401, the first sideband 401 with the marker band 200, the marker band 200 with the second sideband 402, and the second sideband 402 with the first catheter section 102A.

Referring to the embodiment (implementation) as depicted in FIG. 5, the radiopacity of the elongated medical catheter 102 is reduced (preferably, only) in or at the near vicinity of the marker band 200 by reducing the proportion of, or entirely omitting, radiopaque materials in that area of the elongated medical catheter 102 located proximate to the marker band 200. As the difference between the radiopacity of the marker band 200 and elongated medical catheter 102 increases, the local contrast (visual) under fluoroscopy (under a medical imaging system) may be improved. The elongated medical catheter 102 may, advantageously, improves the visibility of the radiopaque features of the elongated medical catheter 102 (by a compatible medical-imaging system), which in turn may lead to easier use, smaller catheters and/or lower X-ray doses, etc. The elongated medical catheter 102 has a decrease in radiopacity at a near vicinity of the marker band 200; this is done in such a way that the difference in radiopacity, between the elongated medical catheter 102 and the marker band 200, is increased (at least in part). For the elongated medical catheter 102 that incorporate radiopaque fillers and/or additives into their materials, this may be achieved by reducing the radiopaque filler content near the marker band 200. The marker band 200 may have an area (zone) with a relatively higher radiopaque filler content.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:
an elongated medical catheter including a marker band with a first sideband and a second sideband, said first and second sidebands are directly attached to opposite sides of the marker band; and
wherein a catheter radiopacity of the elongated medical catheter and a marker band radiopacity of the marker band are different from a radiopacity of the first sideband and the second sideband, the radiopacity of the first sideband being less than the catheter radiopacity and the radiopacity of the second sideband being less than the marker band radiopacity.

2. The apparatus of claim 1, wherein:
the elongated medical catheter defines a catheter lumen extending through the sidebands and the marker band.

3. The apparatus of claim 1, wherein:
the catheter radiopacity decreases near the marker band.

4. The apparatus of claim 3, wherein:
a proportion of radiopaque materials in the elongated medical catheter near the marker band is reduced.

5. The apparatus of claim 3, wherein:
radiopaque materials are omitted in the elongated medical catheter near the marker band.

6. An apparatus, comprising:
an elongated medical catheter having a catheter distal portion and a catheter proximal portion, the catheter having a catheter radiopacity;
a marker band having a first end portion and a second end portion and being positioned between the catheter distal portion and the catheter proximal portion, the marker band having a marker band radiopacity;
a first sideband having a first sideband radiopacity and being directly bonded to the first end portion of the marker band; a second sideband having a second sideband radiopacity and being directly boned to the second end portion of the marker band;
wherein the first sideband radiopacity is less than the catheter radiopacity and the second sideband radiopacity is less than the marker band radiopacity, and wherein the catheter radiopacity decreases near the marker band.

7. The apparatus of claim 6, wherein:
the elongated medical catheter defines a catheter lumen extending through the first sideband, the second sideband and the marker band.

8. The apparatus of claim 6, wherein:
the catheter radiopacity of the elongated medical catheter is less than the radiopacity of the marker band.

9. The apparatus of claim 6, wherein:
a proportion of radiopaque materials in the elongated medical catheter near the marker band is reduced.

10. The apparatus of claim 6, wherein:
radiopaque materials are omitted in the elongated medical catheter near the marker band.

11. The apparatus of claim 6, wherein:
the elongated medical catheter includes a first catheter section and a second catheter section; and
the first catheter section is positioned proximate to the first sideband; and
the second catheter section is positioned proximate to the second sideband.

12. The apparatus of claim 11, wherein:
the elongated medical catheter defines a catheter lumen extending through the first sideband, the second sideband, the marker band, the first catheter section and the second catheter section.

13. A method of using an elongated medical catheter, the method including:
providing the elongated medical catheter having a marker band and first and second sidebands, said first and second sidebands are directly attached to opposite sides of the marker band, each of the elongated medical catheter and the marker band having a radiopacity being different from a radiopacity of the first sideband and the second sideband, the radiopacity of the first sideband being less than the radiopacity of the elongated medical catheter and the radiopacity of the second sideband being less than the radiopacity of the marker band, and the radiopacity of the elongated medical catheter decreasing near the marker band; and
operably coupling the elongated medical catheter with a compatible medical-imaging system.

14. The method of claim 13, wherein:
a proportion of radiopaque materials in the elongated medical catheter near the marker band is reduced.

15. The method of claim 13, wherein:
radiopaque materials are omitted in the elongated medical catheter near the marker band.

* * * * *